(12) United States Patent
Matichuk et al.

(10) Patent No.: US 11,183,303 B2
(45) Date of Patent: Nov. 23, 2021

(54) WEARABLE HEALTH MONITORS AND METHODS OF MONITORING HEALTH

(71) Applicant: Salu Design Group Inc., Edmonton (CA)

(72) Inventors: Bruce Matichuk, Edmonton (CA); Randy Duguay, Edmonton (CA); William Parker, Edmonton (CA); Mathew Moore, Edmonton (CA); Tim Antoniuk, Edmonton (CA)

(73) Assignee: SALU DESIGN GROUP INC., Edmonton (CA)

( * ) Notice: Subject to any disclaimer, the term of this patent is extended or adjusted under 35 U.S.C. 154(b) by 141 days.

(21) Appl. No.: 15/768,363

(22) PCT Filed: Oct. 13, 2016

(86) PCT No.: PCT/CA2016/051195
§ 371 (c)(1),
(2) Date: Apr. 13, 2018

(87) PCT Pub. No.: WO2017/063086
PCT Pub. Date: Apr. 20, 2017

(65) Prior Publication Data
US 2018/0301224 A1 Oct. 18, 2018

Related U.S. Application Data

(60) Provisional application No. 62/240,607, filed on Oct. 13, 2015.

(51) Int. Cl.
*G16H 50/20* (2018.01)
*G06N 20/00* (2019.01)
(Continued)

(52) U.S. Cl.
CPC .......... *G16H 50/20* (2018.01); *A61B 5/0205* (2013.01); *A61B 5/165* (2013.01); *A61B 5/4806* (2013.01);
(Continued)

(58) Field of Classification Search
CPC ... G06F 1/00–2221/2153; G16H 10/00–80/00; A61B 1/00–2576/026;
(Continued)

(56) References Cited

U.S. PATENT DOCUMENTS 9,426,275 B2 * 8/2016 Eim ...................... G06F 3/0416
10,278,592 B2 * 5/2019 Fish .................... A61B 5/02055
(Continued)

FOREIGN PATENT DOCUMENTS

| CN | 203261079 | * 10/2013 | ............... H02J 7/00 |
| EP | 1965696 A2 | 9/2008 | |
| JP | 2012518515 A | 8/2012 | |

OTHER PUBLICATIONS

Thomas et al., "BioWatch—A Wrist Watch based Signal Acquisition System for Physiological Signals including Blood Pressure," IEEE, pp. 2286-2289. (Year: 2014).*

(Continued)

*Primary Examiner* — Elaine Gort
*Assistant Examiner* — Jonathon A. Szumny
(74) *Attorney, Agent, or Firm* — Edlavitch Law PLLC

(57) ABSTRACT

Wearable technologies, such as wearable health monitors, and methods of use are provided. In some embodiments, the wearable technology can be worn at the wrist of an individual and can use an accelerometer, pulse oximeter, and electrocardiogram to measure heart rate, oxygen saturation, blood pressure, pulse wave velocity, and activity. This information can then be provided to the individual. The individual can alter their behaviors and relationships with (Continued)

their own health by using features such as notifications and auto-tagging to better understand their own stress, diet, sleep, and exercise levels over various time periods and subsequently make appropriate behavioral changes.

29 Claims, 4 Drawing Sheets

(51) Int. Cl.
*G16H 40/63* (2018.01)
*A61B 5/0205* (2006.01)
*A61B 5/16* (2006.01)
*A61B 5/00* (2006.01)
*G06K 19/077* (2006.01)
*A61B 5/021* (2006.01)
*A61B 5/024* (2006.01)
*A61B 5/11* (2006.01)
*A61B 5/145* (2006.01)
*A61B 5/1455* (2006.01)
*A61B 5/0295* (2006.01)
*A61B 5/318* (2021.01)
*A61B 5/332* (2021.01)
*A61B 5/026* (2006.01)

(52) U.S. Cl.
CPC ............ *A61B 5/4866* (2013.01); *A61B 5/681* (2013.01); *A61B 5/7264* (2013.01); *A61B 5/7267* (2013.01); *A61B 5/7282* (2013.01); *G06K 19/07762* (2013.01); *G06N 20/00* (2019.01); *G16H 40/63* (2018.01); *A61B 5/0059* (2013.01); *A61B 5/021* (2013.01); *A61B 5/026* (2013.01); *A61B 5/0295* (2013.01); *A61B 5/02108* (2013.01); *A61B 5/02416* (2013.01); *A61B 5/02438* (2013.01); *A61B 5/1118* (2013.01); *A61B 5/1455* (2013.01); *A61B 5/14542* (2013.01); *A61B 5/14551* (2013.01); *A61B 5/318* (2021.01); *A61B 5/332* (2021.01); *A61B 5/6814* (2013.01); *A61B 5/6826* (2013.01); *A61B 5/6829* (2013.01); *A61B 5/6831* (2013.01); *A61B 5/7221* (2013.01); *A61B 2562/0219* (2013.01)

(58) Field of Classification Search
CPC ..... G06K 1/00–2215/111; G06N 3/00–99/007
See application file for complete search history.

(56) References Cited

U.S. PATENT DOCUMENTS

| | | | |
|---|---|---|---|
| 2006/0258921 A1* | 11/2006 | Addison | A61B 5/6829 600/323 |
| 2010/0056880 A1* | 3/2010 | Cho | A61B 5/00 600/301 |
| 2010/0217099 A1* | 8/2010 | LeBoeuf | A61B 5/486 600/301 |
| 2013/0106684 A1* | 5/2013 | Weast | A63B 71/0622 345/156 |
| 2014/0024957 A1* | 1/2014 | Kim | A61B 5/72 600/490 |
| 2014/0073486 A1* | 3/2014 | Ahmed | A61B 5/681 482/9 |
| 2014/0275850 A1* | 9/2014 | Venkatraman | A61B 5/4812 600/301 |
| 2015/0126824 A1 | 5/2015 | LeBoeuf et al. | |
| 2015/0297134 A1* | 10/2015 | Albert | A61B 5/681 600/384 |
| 2015/0320328 A1* | 11/2015 | Albert | A61B 5/0402 600/480 |
| 2016/0117466 A1* | 4/2016 | Singh | G06Q 50/265 702/19 |
| 2016/0128586 A1* | 5/2016 | Parton | A61B 5/02405 600/479 |
| 2016/0183812 A1* | 6/2016 | Zhang | A61B 5/117 600/301 |
| 2016/0256116 A1* | 9/2016 | Baik | A61B 5/7278 |
| 2016/0367987 A1* | 12/2016 | Arbabian | G01N 33/48792 |
| 2017/0020444 A1* | 1/2017 | Lurie | A61B 5/6898 |
| 2017/0039480 A1* | 2/2017 | Bitran | G06N 20/00 |
| 2017/0243385 A1* | 8/2017 | Mitsugi | A44C 5/00 |
| 2018/0085011 A1* | 3/2018 | Ma | A61B 5/7203 |
| 2018/0275715 A1* | 9/2018 | Park | G06F 1/1652 |
| 2019/0005367 A1* | 1/2019 | Yamada | G06K 19/07749 |
| 2019/0104951 A1* | 4/2019 | Valys | A61B 5/7267 |
| 2019/0167902 A1* | 6/2019 | Kamen | G16H 10/65 |
| 2019/0320916 A1* | 10/2019 | Banet | A61B 5/02416 |

OTHER PUBLICATIONS

First Examination Report (FER) issued by the Indian Patent Office (IPO) dated Apr. 22, 2021 for Indian Patent Application No. 201827017757.

* cited by examiner

WEARABLE HEALTH MONITORS AND METHODS OF MONITORING HEALTH

CROSS-REFERENCE TO RELATED APPLICATIONS

This application claims the benefit of U.S. Provisional Patent Application Ser. No. 62/240,607, filed Oct. 13, 2015, the entirety of which is incorporated herein by reference.

FIELD OF THE DISCLOSURE

The present disclosure is related to wearable technologies and, more particularly, to wearable health monitors and methods of monitoring health.

BACKGROUND

There has been a decline in the overall health status of the general population. Metabolic syndrome (i.e. the combined effects of obesity, diabetes, hypertension, and dyslipidemia) and its components have been increasing throughout the past twenty years, mostly due to worsening diets, poor exercise levels, personal stress, and reduced or poor sleep patterns. Additionally, individuals have poor relationships with their own health.

There have been attempts to address these issues by providing the health monitoring of an individual. Existing attempts, however, have their shortcomings and the behavior of the monitored individuals remain unchanged. In most cases, insufficient information is provided to the individual, the information is not communicated to the individual in an appropriate/efficient way, the individual may not easily relate or understand how the information impacts them personally, and/or the individual is not able to provide input into the system in order to customize the information. As such, the individual's behavior remains unchanged and without behavioral change, the health and/or well-being of the individual does not improve or, in many cases, worsens.

Accordingly, there remains a need to provide health monitors and methods of monitoring health and wellness that can overcome the shortcomings of the prior art.

SUMMARY

Wearable technologies, such as wearable health monitors, and methods of use are provided. In some embodiments, the wearable technology can be worn at the wrist of an individual and can use an accelerometer, pulse oximeter, and electrocardiogram to measure heart rate, oxygen saturation, blood pressure, pulse wave velocity, and activity. This information can then be provided to the individual. The individual can alter their behaviors and relationships with their own health by using features such as notifications and auto-tagging to better understand their own stress, diet, and exercise levels over various time periods and subsequently make appropriate behavioral changes.

In some embodiments, a wearable electronic apparatus is provided, the apparatus to be worn around an individual's wrist in order to monitor and assess the individual's cardiovascular health, the apparatus comprising: a band comprising an electronics module configured to position the electronics module proximate a distal radial artery portion of the individual's wrist, the electronics module an accelerometer for taking accelerometer readings from the wrist to be converted into an activity rating; and an electrocardiogram (ECG) and a pulse oximeter sensor with photoplethysmography (PPG) for taking heart rate, pulse wave velocity (PWV), and oxygen saturation readings from the wrist to be converted into blood pressure ratings; a processor module in communication with the electronics module to implement an algorithm to convert the PWV readings into estimated blood pressure measurements and for converting the readings and ratings into outputs (health assessments and/or health recommendations); and an output/display module in communication with the processor module for reflecting any of the readings, ratings, and/or outputs to the individual.

In some embodiments, the apparatus can be retrofit to existing wearable technologies, for example, the apparatus can comprise a wristband peripheral, to be retrofit to a watch, a smartwatch, or other complimentary wrist-worn wearable technology.

In some embodiments, the apparatus can be activated or deactivated by the individual contacting the electronics module with one finger from the opposite hand that the wrist is being worn on. The contact of the finger on one side of the apparatus in combination with the contact of the wrist with the other side of the apparatus can complete an electronic circuit.

In some embodiments, the output of the data readings and analysis can provide a health trajectory for the individual to predict a future state of health, as well as review the historical health trajectory from past states.

In some embodiments, the output of the data readings and analysis can be subject to an "autotagging" program where the apparatus can determine the individual's behavior (such as eating, sleeping, exercising, or a state of stress) at a time point and attaching an electronic tag to that event. The auto-tagging program can also include a means whereby manual data can also augment and increase the individual's ability to capture additional details of personal relevance.

In some embodiments, the data collected and amalgamated through the apparatus can be subject to "machine learning" methodologies to provide for predictive analysis for the individual to assist the individual in achieving personal health and wellness objectives.

In some embodiments, the data collected by the apparatus can apply psychometrics data analysis to assist the individual in achieving personal health and wellness objectives.

Broadly stated, in some embodiments, a wearable electronic apparatus is provided, the apparatus to be worn around an individual's wrist in order to monitor and assess the individual's cardiovascular health, the apparatus comprising: a band comprising an electronics module, the band configured to position the electronics module proximate a distal radial artery portion of the individual's wrist, the electronics module comprising, an accelerometer for taking accelerometer readings from the wrist to be converted into an activity rating; and an electrocardiogram (ECG) and a pulse oximeter sensor with photoplethysmography (PPG) for taking heart rate, pulse wave velocity (PWV), pulse transit time (PTT), and oxygen saturation readings from the wrist to be converted into blood pressure ratings; a processor module in communication with the electronics module to implement an algorithm to convert the ECG and PWV readings into blood pressure and for converting the readings and ratings into outputs (health assessments and/or health recommendations); and an output/display module in communication with the processor module for reflecting any of the readings, ratings, and/or outputs to the individual.

In some embodiments, the output/display module is integral with the electronics module. In some embodiments, the output/display module is remote, but in communication with the electronics module. In some embodiments, the output/ display module is a multi-color LED for providing individual interaction with device. In some embodiments, the multi-color LED is configured to let the individual know if ECG, pulse oximeter, and accelerometer are ready to obtain the readings, if the apparatus is converting the readings to the outputs, and if the apparatus has successfully completed each measurement. In some embodiments, the band further comprises a connection to receive a smartwatch. In some embodiments, the connection is a smartwatch pin connection.

Broadly stated, in some embodiments, a method is provided for monitoring and assessing an individual's cardiovascular health, the steps of the method comprising providing a wearable electronic apparatus as described herein; positioning the electronics module proximate the distal radial artery portion of a wrist of an individual; taking simultaneous measurements of activity, heart rate, PWV, and oxygen saturation; using the processor to convert the heart rate and PWV measurements into a blood pressure reading; and reflecting any of the readings, ratings, and/or outputs to the individual through the output/display module.

In some embodiments, the taking of the simultaneous measurements step is accomplished by using a finger of one hand of the individual to touch the wearable electronic apparatus on wrist of other hand to complete the ECG circuit and record the simultaneous measurements. In some embodiments, the output of the data readings and analysis can be subject to an auto-tagging and/or tagging program where the apparatus can determine the individual's behavior as an event (such as eating, sleeping, working out, or stress) at a time point and attach an electronic/digital tag to that event. In some embodiments, the output of the data readings and further analysis can provide a health trajectory for the individual to predict a future state of health.

According to one aspect of this disclosure, there is provided a wearable electronic apparatus for monitoring a user's cardiovascular health. The apparatus comprises: an attachment structure for attaching the wearable apparatus to a predefined body location of the user; and an electronics module coupled to the attachment structure. The electronics module comprises: a plurality of sensors comprising at least an electrocardiogram (ECG) sensor for measuring data including at least one of the heart rate, pulse wave velocity (PWV), pulse transit time (PTT), and a pulse oximeter sensor with photoplethysmography (PPG) for measuring oxygen saturation of the user; a processor module coupled to the plurality of sensors for collecting data therefrom and for calculating blood pressure using a machine learning method based at least one collected data; and an output module coupled to the processor module outputting at least one of the calculated blood pressure and the collected data.

In some embodiments, the pulse oximeter sensor comprises a Pulse LED and a light sensor.

In some embodiments, the Pulse LED is configured to emit a first light at a first wavelength and a second light at a second wavelength, and wherein the light sensor is configured to receive at least a portion of the first light reflected from a skin of the user and at least a portion of the second light reflected from a skin of the user.

In some embodiments, the first wavelength is about 660 nm and the second wavelength is about 940 nm.

In some embodiments, the electronics module further comprises an accelerometer for collecting the movement data of the user.

In some embodiments, the processor module calculates blood pressure using the machine learning method based on collected data and the user's historical health data.

In some embodiments, the machine learning method is a polynomial regression analysis method, a neural network, a Bayesian network, a decision tree, an adaptive logic network, or a support vector machines.

In some embodiments, the attachment structure is a band.

In some embodiments, the band is configured to position the wearable electronic apparatus on a wrist of the user.

In some embodiments, the band is configured to position the electronics module in proximity with a blood vessel of the user.

In some embodiments, the blood vessel is a distal radial artery.

In some embodiments, the output module is a display on the wearable electronic apparatus.

In some embodiments, the display is a multi-color LED.

In some embodiments, the display is configured to notify the user if the plurality of sensors are ready to obtain readings, if the wearable electronic apparatus is converting the readings to output data, and if the wearable electronic apparatus has successfully completed collection of data from the sensors.

In some embodiments, the output module comprises a communication component for transmitting at least one of the calculated blood pressure and the collected data to a device external to the wearable electronic apparatus.

In some embodiments, the communication component is a wireless communication module.

In some embodiments, the wireless communication module is a Bluetooth module.

In some embodiments, the attachment structure further comprises a connection for receiving a smartwatch.

In some embodiments, the connection is a pin connection.

In some embodiments, the electronics module further comprises at least one circuit board, a battery and a battery charging circuit.

According to another aspect of this disclosure, there is provided a method for monitoring a user's cardiovascular health. The method comprises: collecting data of the user using at least one sensor, said data comprising at least one of the heart rate, pulse wave velocity (PWV), pulse transit time (PTT), and oxygen saturation; calculating blood pressure of the user using a machine learning method based at least one collected data; and outputting at least one of the calculated blood pressure and the collected data.

In some embodiments, the collecting data step comprises: collecting at least one of the heart rate, pulse wave velocity (PWV), pulse transit time (PTT) of the user using at least an electrocardiogram (ECG) sensor; and collecting oxygen saturation of the user using a pulse oximeter sensor with photoplethysmography (PPG).

In some embodiments, collecting oxygen saturation of the user using a pulse oximeter sensor comprises: emitting a first light at a first wavelength and a second light at a second wavelength; receiving at least a portion of the first light reflected from a skin of the user and at least a portion of the second light reflected from a skin of the user; determining a first reading corresponding to the amount of the first light being absorbed by the blood under the skin and a second reading corresponding to the amount of the second light being absorbed by the skin; and calculating the oxygen saturation of the user using the ratio between the first and second readings.

In some embodiments, the first wavelength is about 660 nm and the second wavelength is about 940 nm.

In some embodiments, the above method further comprises: collecting the movement data of the user using an accelerometer.

In some embodiments, the calculating blood pressure step comprises: calculating blood pressure using the machine learning method based on collected data and the user's historical health data.

In some embodiments, the machine learning method is a polynomial regression analysis method, a neural network, a Bayesian network, a decision tree, an adaptive logic network, or a support vector machines.

In some embodiments, the above method further comprises: attaching the at least one sensor on a wrist of the user.

In some embodiments, the attaching step comprises: attaching the at least one sensor on the wrist of the user using a band.

In some embodiments, the attaching step comprises: attaching the at least one sensor on the wrist of the user in proximity with a blood vessel of the user.

In some embodiments, the blood vessel is a distal radial artery.

In some embodiments, the outputting step comprises: displaying at least one of the calculated blood pressure and the collected data.

In some embodiments, the displaying step comprises: displaying at least one of the calculated blood pressure and the collected data using a multi-color LED.

In some embodiments, the displaying step comprises: notifying the user if the at least one sensor is ready to obtain readings, if the readings are being converted to output data, and if collection of data from the sensors has been successfully completed.

In some embodiments, the outputting step comprises: transmitting at least one of the calculated blood pressure and the collected data to a remote device. In some embodiments, the transmitting step comprises: wirelessly transmitting at least one of the calculated blood pressure and the collected data to the remote device.

In some embodiments, the transmitting step comprises: transmitting at least one of the calculated blood pressure and the collected data to the remote device using Bluetooth.

In some embodiments, the above method further comprises: attaching the at least one sensor about a smartwatch.

In some embodiments, attaching the at least one sensor about the smartwatch comprises: attaching the at least one sensor about the smartwatch using a pin connection.

According to another aspect of this disclosure, there is provided a system for monitoring a user's cardiovascular health. The system comprises: an attachment structure for attaching the wearable apparatus to a predefined body location of the user; an electronics module coupled to the attachment structure; and a device external to the attachment structure. The electronics module comprises: a plurality of sensors comprising at least an electrocardiogram (ECG) sensor for measuring data including at least one of the heart rate, pulse wave velocity (PWV), pulse transit time (PTT), and a pulse oximeter sensor with photoplethysmography (PPG) for measuring oxygen saturation of the user; a processor module coupled to the plurality of sensors for collecting data therefrom and; and an output module coupled to the processor module outputting at least one of collected data to the external device. The external device calculates blood pressure using a machine learning method based at least one data received from the output module.

In some embodiments, the pulse oximeter sensor comprises a Pulse LED and a light sensor.

In some embodiments, the Pulse LED is configured to emit a first light at a first wavelength and a second light at a second wavelength, and wherein the light sensor is configured to receive at least a portion of the first light reflected from a skin of the user and at least a portion of the second light reflected from a skin of the user.

In some embodiments, the first wavelength is about 660 nm and the second wavelength is about 940 nm.

In some embodiments, the electronics module further comprises an accelerometer for collecting the movement data of the user.

In some embodiments, the processor module calculates blood pressure using the machine learning method based on collected data and the user's historical health data.

In some embodiments, the machine learning method is a polynomial regression analysis method, a neural network, a Bayesian network, a decision tree, an adaptive logic network, or a support vector machines.

In some embodiments, the attachment structure is a band.

In some embodiments, the band is configured to position the wearable electronic apparatus on a wrist of the user.

In some embodiments, the band is configured to position the electronics module in proximity with a blood vessel of the user.

In some embodiments, the blood vessel is a distal radial artery.

In some embodiments, the output module is a display on the wearable electronic apparatus.

In some embodiments, the display is a multi-color LED.

In some embodiments, the display is configured to notify the user if the plurality of sensors are ready to obtain readings, if the wearable electronic apparatus is converting the readings to output data, and if the wearable electronic apparatus has successfully completed collection of data from the sensors.

In some embodiments, wherein the output module comprises a communication component for transmitting at least one of the calculated blood pressure and the collected data to a device external to the wearable electronic apparatus.

In some embodiments, the communication component is a wireless communication module.

In some embodiments, the wireless communication module is a Bluetooth module.

In some embodiments, the attachment structure further comprises a connection for receiving a smartwatch.

In some embodiments, the connection is a pin connection.

In some embodiments, the electronics module further comprises at least one circuit board, a battery and a battery charging circuit.

DETAILED DESCRIPTION

Wearable technologies, such as wearable health monitors, and methods of use are provided.

In some embodiments, the wearable technology can be worn at the wrist of an individual and can use an accelerometer, pulse oximeter, and electrocardiogram to measure heart rate, oxygen saturation, blood pressure, pulse wave velocity, and activity. This information can then be provided to the individual. The individual can alter their behaviors and relationships with their own health by using features such as notifications and auto-tagging and/or manual tagging, machine learning, artificial intelligence, psychometric analysis, and predictive analytics, to better understand their own stress, diet, and exercise levels over various time periods and subsequently make appropriate behavioral changes.

Figure 1:
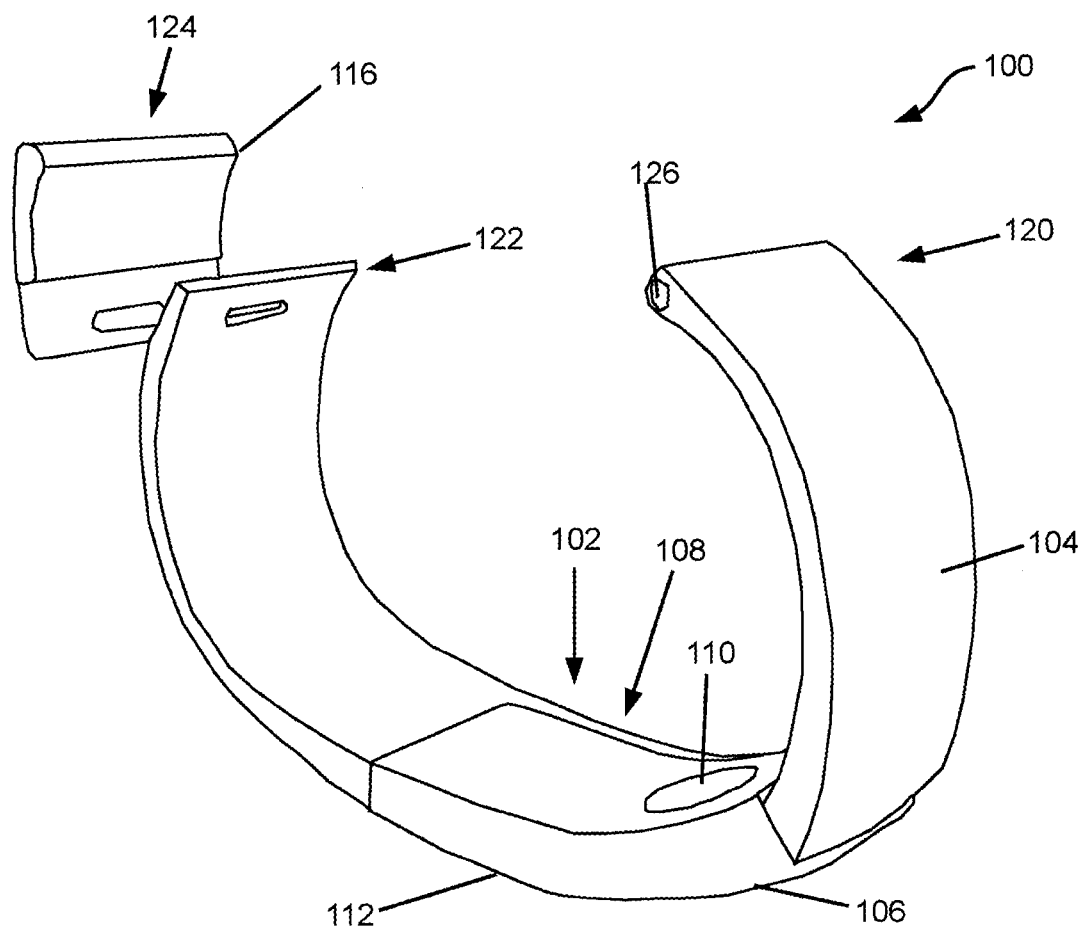
FIG. 1 is a perspective view of an embodiment of a wearable electronic apparatus for monitoring and assessing an individual's cardiovascular health.

Referring now to FIG. 1, an embodiment of a wearable apparatus is shown and generally referred using the numeral 100. The wearable apparatus comprises an electronics module 102 and an attachment structure 104 such as a band for attaching the wearable apparatus 100 to a user's wrist. In this embodiment, the electronics module 102 is housed within a hard case 106, and comprises a circuit board, for example a printed circuit board (PCB) 108 for collecting data from a plurality of sensors (described later) for monitoring a user's health metrics.

The band 104 in this embodiment is soft or flexible case, and may house other components of apparatus 100. For example, in this embodiment, the band 104 comprises openings for a light sensor 110 housed therein, and one or more sensors such as an electrocardiogram (ECG) electrodes 112 for acquiring a signal of electrical activity through the user's heart. In this embodiment, the band 104 comprises two ECG electrodes 112, one touching an anterior portion of the user's wrist, and the other to be touched by the user's opposing hand's finger to complete a circuit across the heart for make a reading.

For example, the user can use a finger of one hand to touch the apparatus 100 that is attached to the wrist of the opposite arm in order to record an ECG signal, and simultaneously initiate a complete set of biometrics as described later. As band 104 can be configured to be positioned on a user's wrist, simultaneous quality measurements of blood pressure, pulse wave velocity, pulse transit time, and oxygen saturation can also be provided.

The band 104 is configured and sized to position electronics module 102 proximate the distal portion of a user's radial artery in order to achieve increased accuracy in electronic readings. In some embodiments, the band 104 is an expandable band for adapting to different sizes of wrists. For example, one or more link pieces 116 may be added to the band 104 to extend the band 104 for larger size wrist.

In some embodiments, the two ends 120 and 122 of the band 104, or the end 120 of the band 104 and the end 124 of the link piece 116, may be coupled to each other wearable apparatus 100 for attaching the wearable apparatus 100 to a user's wrist. In some other embodiments, the band 104 may be configured to receive a smartwatch (not shown) through a connection 126, for example, but not limited to a smartwatch pin connection to connect to the smartwatch. In some embodiments, connection 126 can be configured to attach to a pre-existing smartwatch female pin connection. In some embodiments, connection 126 can be integrally built into band 104. Accordingly, the wearable apparatus 100 and smartwatch can be worn as a single wearable device, wherein the apparatus 100 acts as a smartband, namely a band comprising smart electronics or a connection to communication with a smart technology, or acts as a peripheral to a smartwatch that can be configured to tie-in with existing smartwatches for the purpose of adding key health metrics that do not currently exist on such smartwatches. Where a health metric, such as the heart rate and pulse measurements, can be provided by the smartwatch, the wearable apparatus 100 can provide an additional measurement to compare to the smartwatch measurement.

Figure 2:
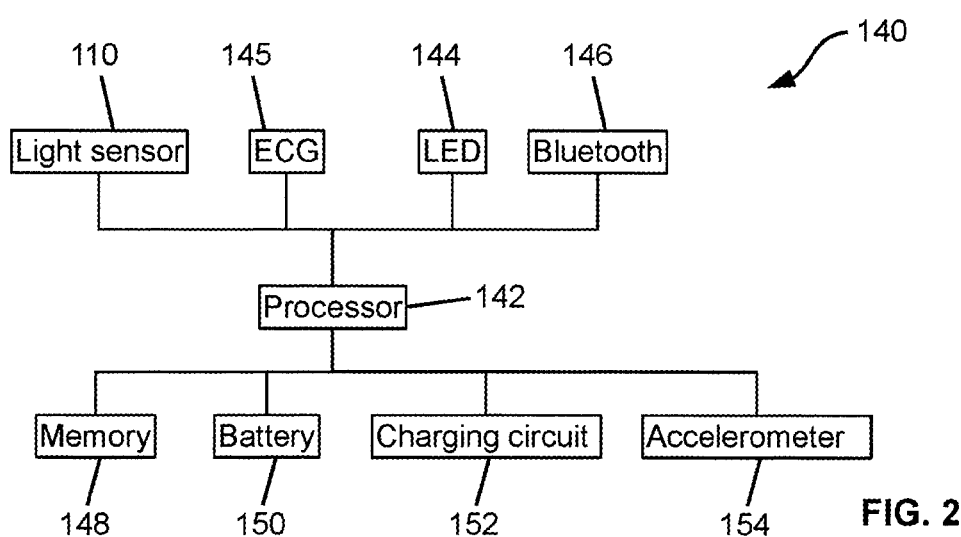
FIG. 2 is a schematic diagram 140 showing the structure of the electrical components of the wearable apparatus.

FIG. 2 is a schematic diagram 140 showing the structure of the electrical components of the wearable apparatus 100. As shown, in this embodiment, the wearable apparatus 100 comprises a processor 142, a light sensor 110, an ECG module 145 connecting to the ECG electrodes 112, pulse LED 144, a wireless communication module 146 such as a Bluetooth module, a memory 148, a battery 150, a charging circuit 152 for charging the battery 150, an accelerometer 154, and necessary circuitry such as a digital circuitry on the PCB 108. The process 142 is in communication with the components 110, and 144 through 154, and controls the operation thereof. The wearable apparatus 100 may also comprise a Bluetooth antenna (not shown) for transmitting and receiving Bluetooth signals.

Figures 3A, 3B:
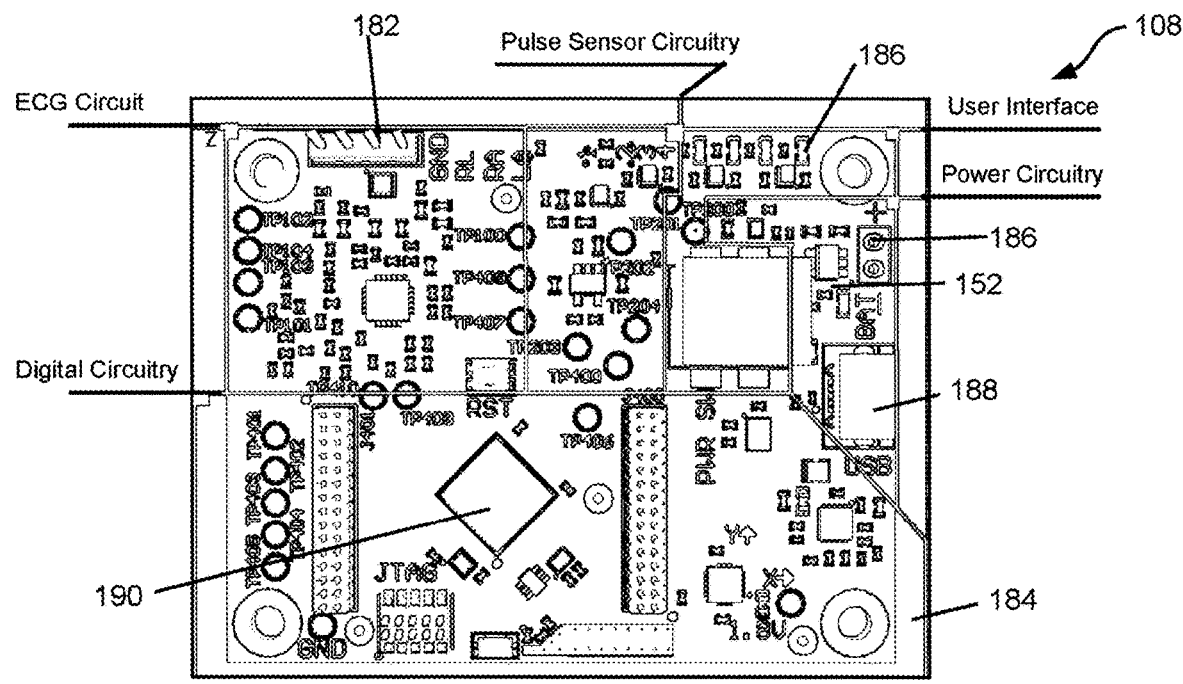
FIG. 3A is a front perspective view of an embodiment of an electronics module for a wearable electronic apparatus for monitoring and assessing an individual's cardiovascular health.
FIG. 3B is a rear perspective view of the embodiment of the electronics module shown in FIG. 2.

Referring now to FIGS. 3A and 3B, an embodiment of the PCB 108 is shown from the front and rear respectively. As shown, the PCB 108 comprises ECG inputs 182 to attach ECG electrodes 112 to the digital circuitry 184. The PCB 108 also comprises LED Indicators 186 to attach one or more LEDs, e.g., four (4) LEDs 186 in the example, for informing the user regarding the status or states of the apparatus 100, such as charging, measurement acquisition, transfer to app processes, and the like. In some embodiments, multi-color LEDs can be used for facilitating user interaction with the apparatus 100. The LEDs 186 are used for indicating to the user if ECG, pulse oximeter, and accelerometer sensors are able to get readings and if the device is converting those reading measurements to the appropriate outputs. Accordingly, feedback on adequacy of the measurements can be provided to the user.

In this embodiment, the PCB 108 comprises, on its front side, a primary energy input 186 for connecting to an power source (not shown), e.g., a battery such as a Lithium battery, for powering the components 110, and 142 through 154 of the apparatus 100. In this embodiment, the PCB 108 further comprises a secondary energy input, such as a charging circuitry 152 and a USB charger input 188, connecting to a secondary power source (not shown) as needed, for charging the battery. In another embodiment, the wearable apparatus 100 may also be powered by the secondary power source via the secondary energy input such that the wearable apparatus 100 is still operable when the battery is being charged.

In this embodiment, the processor 142, the Bluetooth module 146 and memory 148 are integrated into one central chip 190 such as a microcontroller, also mounted to the front side of the PCB 108.

On its rear side, the PCB 108 comprises a Pulse LED 144 to provide two different light sources, with one at a wavelength of about 660 nm (red light) and the other at a wavelength of about 940 nm (infrared light), and a light sensor 110 to acquire the light emitted from the Pulse LED 144 and reflected off of a peripheral artery. In this embodiment, light sensor 110 also comprises two separate light sensing components corresponding to the two light sources of the Pulse LED 144, including one light sensing component at about 660 nm and another light sensing component at about 940 nm. Alternatively, the light sensor 110 may be a single sensor capable of acquiring both 660 nm and 940 nm wavelengths. The Pulse LED 144 and light sensor 110 can be used for pulse oximetry, forming a pulse oximeter with photoplethysmography (PPG). Pulse oximetry works by comparing a first reading corresponding to the amount of light absorbed by the blood under the skin at one wavelength, for example about 660 nm, corresponding to oxygenated blood, and a second reading corresponding to the amount of light absorbed by the blood under the skin at a second wavelength, for example about 940 nm, corresponding to deoxygenated blood. The ratio between the two readings can determine how much oxygen is present in the user's blood and can also called oxygen saturation.

In this embodiment, the Pulse LED 144 and light sensor 110 are adjacent to each other on the PCB 108, and are located in the wearable apparatus 100 such that, when a user wears the wearable apparatus 100 on a wrist thereof, the Pulse LED 144 and light sensor 110 are in proximity with the radial artery. In this manner, the light emitted from the Pulse LED 144 is reflected by the skin close to the radial artery and received by the light sensor 110. The light received by the light sensor 110 then contains more detailed information about the user's health metrics, compared to that when the Pulse LED 144 and light sensor 110 are at other locations of the wearable apparatus 100.

In some embodiments, the PCB 108 can also include an accelerometer 154 for activity tracking by assessing the movement that the apparatus 100 experiences. In some embodiments, the accelerometer 154 can be incorporated into the central chip 190. In some embodiments, an accelerometer measurement can be acquired from an external accelerometer such as from a connected smartwatch that has a built-in accelerometer.

In this embodiment, the processor 142 executes machine executable code implementing a built-in device algorithm for computing basic health metrics such as heart rate. In some embodiments, the code of the device algorithm is stored in the memory 148. The memory 148 also stores basic data collected from the above described sensors.

As described above, the central chip 190 integrates a Bluetooth component 146. The Bluetooth component 146 transmits data to and from external devices such as smartphones, tablets, laptops, desktops and the like.

In operation, the wearable apparatus 100 can be configured to provide a user with feedback regarding their health metrics and health behaviors. In particular, the wearable apparatus 100 collects data or measurements from the pulse oximeter, ECG, and accelerometer to provide heart rate, oxygen saturation, pulse wave velocity, blood pressure, and activity measurements.

In some embodiments, the sensor measurements can be inputted into the circuitry on the PCB 108 via the ECG inputs 182 from the ECG electrodes 112, from the light sensor 110 receiving reflected light from the Pulse LED 144, and the accelerometer 154 (or an external accelerometer as described above). Such sensor measures may be stored in the memory 148, and may be used by the processor 142 for basic computing using the device algorithm to obtain basic health metrics such as heart rate.

In some embodiments, ECG and pulse oximetry readings are combined to obtain the pulse wave velocity (PWV), which can then be used to calculate a blood pressure value. In order to do this the R-wave of the ECG signal can be compared with the onset of the blood pulse sensed by the pulse oximeter. In some embodiments, a portion of the device algorithm can help to find these two points differentiated in time. Known estimates of distances between a person's heart and wrist from anthropometric data can help determine the distance between these two positions. By dividing the distance over the time, the PWV can be calculated. Then, various factors including, but not limited to, age, gender, smoking history, alcohol history, blood sugar control, activity, sleep, heart rate, and diet can be factored into an estimate of the user's blood pressure.

In one embodiment, the processor 142 uses an algorithm implementing a method described in the academic paper "Continuous blood pressure measurement by using the pulse transit time: comparison to a cuff-based method" to Heiko Gesche, Detlef Grosskurth, Gert Küchler and Andreas Patzak, published on Eur J Appl Physiol. 2012 January; 112 (1):309-15, the content of which is incorporated herein by reference in its entirety. The method uses Pulse transit time (PTT) and pulse wave velocity (PWV) for monitoring blood pressure.

In some embodiments, the wearable apparatus 100 uses machine learning to process the data collected from various sensors to provide for predictive analysis for the user to assist the user in achieving personal health and wellness objectives.

For example, the wearable apparatus 100 uses a supervised learning method for calculating and predicting blood pressure as follows.

In this method, data is in sets of PTT and Other Markers. The method uses a suitable machine learning method, such as machine learning method may be a polynomial regression analysis method, a neural network, a Bayesian network, a decision tree, an adaptive logic network, a support vector machines or the like, for function learning. Training output for each recording includes a value for Systolic blood pressure and a value for Diastolic blood pressure.

In predicting blood pressure using PTT and other markers, the vascular system follows a physical model of a pump that pumps a fluid of a particular viscosity into a tube of a particular length and width with a specific wall elasticity, the amount of time it takes for a fluid pressure wave to travel through the tube can be calculated by the Moens-Korteweg equation:

$$PWV = \text{sqrt}((E_{inc} * h)/2r\rho)$$

where sqrt(x) representing the square root of x, $E_{inc}$ is the incremental modulus of stiffness, h is vessel wall thickness, r is the vessel radius, ρ is the density of blood, and PWV is the pulse wave velocity.

Based on the Moens-Korteweg equation, a probabilistic model may be established using PTT and Other Markers as probabilistic predictors of Systolic blood pressure (SBP) and diastolic blood pressure (DBP). SBP and DBP are random variables, the values of which are determined by other variables include PTT, height, weight, ethnicity, age, gender, Pulse Wave Characteristics and the like. Herein, PTT is the amount of time it takes for the heart to start pumping and for the pump pulse to reach the radial artery. Ethnicity is a number or index used to distinguish different data sets. Pulse Wave Characteristics include a variety of values derived from standard PPG pulse wave analysis.

Pulse wave analysis is known, for example, the academic paper "On the Analysis of Fingertip Photoplethysmogram Signals", to Mohamed Elgendi, published on Current Cardiology Reviews, 2012, 8, 14-25, the content of which is incorporated herein by reference in its entirety, provides a detailed description of pulse wave analysis.

By using pulse wave analysis, basic pulse wave characteristics may be obtained, including the systolic peak, diastolic peak, peak difference, dicrotic notch, and pulse width. In this embodiment, the supervised learning method uses these characteristics along with Pulse Transit Time, Heart Rate, Heart Rate Variability, and optionally other recorded values to generate SBP vs DBP values based on a machine learned mapping function. Using more data increases the accuracy and reliability of the blood pressure calculation.

The method uses ECG to detect the start of the heart beat and PPG to detect the point at which the pulse reaches the radial artery. While the ECG or PPG measuring location in the method disclosed herein is relatively far from the heart, Applicant's test results show that, the method is insensitive to the specific distance between the ECG or PPG measuring location and the heart, or the specific point at which the ECG or PPG is measured, as long as the measurement is consistent, the measurement results or readings are about the same for the same person at about the same body conditions during different measurements.

In one embodiment, the polynomial regression analysis may be used to generate a mapping function. As is known in the art and described in Wikipedia, polynomial regression is a statistic method with a form of linear regression in which the relationship between the independent variable x and the dependent variable y is modelled as an n-th degree polynomial. Polynomial regression fits a nonlinear relationship between the value of x and the corresponding conditional mean of y, denoted $E(y|x)$, and has been used to describe nonlinear phenomena. The regression function $E(y|x)$ is linear in the unknown parameters that are estimated from the data.

Those skilled in the art appreciate that, in various embodiments, any machine learning technique will work to produce a viable function map.

The supervised learning method assumes a particular polynomial degree and attempts to learn an equation by considering multiple examples.

For example, for EBP using 3 unknowns, $$EBP = A*PTT^2 + B*PTT + C,$$

where A, B and C are unknowns. Given 3 examples that include an EBP value and a PTT value, the values of A, B and C are then solved.

The supervised learning method uses multiple training points to find a closer fit. In order to make the function more reliable regression can be used to consider multiple points along the curve.

As those skilled in the art appreciate, polynomial regression analysis is one form of function fitting, and other machine learning algorithms can be alternatively used to generate alternative function maps. For example, in another embodiment, neural network analysis may be used.

As defined by Dr. Robert Hecht-Nielsen in "Neural Network Primer: Part I" by Maureen Caudill, AI Expert, February 1989, a neural network is a computing system made up of a number of simple, highly interconnected processing elements, which process information by their dynamic state response to external inputs. Neural networks are typically organized in layers. Layers are made up of a number of interconnected "nodes" containing an "activation function".

In the neural network analysis disclosed herein, the retinal layer is represented by the inputs. The function map is then modeled using multiple hidden layers. The final layer may be modeled as a collection of neurons representing the range of output. Alternatively, the final layer may be a single neuron with an output intensity that maps to a particular DBP or SBP value.

Figure 4A:
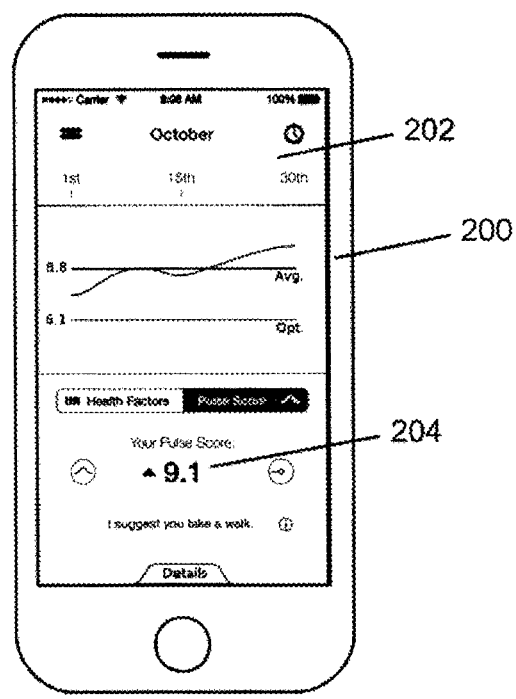
FIGS. 4A and 4B show a front elevation view of embodiments of an electronic App for monitoring and assessing an individual's cardiovascular health, as depicted on an embodiment of a smartphone or other display device.
Figure 4B:
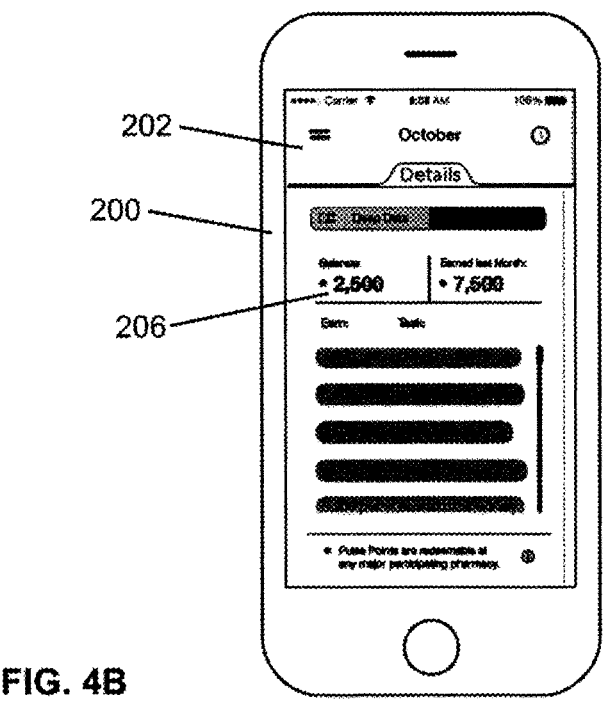

In some embodiments, the wearable apparatus 100 may be configured to send the sensor readings/measurements and processor-calculated data through the Bluetooth 146 to external devices such as smartphones, tablets, laptops, desktops and the like. As shown in FIGS. 4A and 4B, an App 202 or a software application is executed on a display device 200 to provide an interactive user experience. The App 202 receives the sensor measurements and processor-calculated data from the wearable apparatus 100 using Bluetooth paired to the Bluetooth 146 of the wearable apparatus 100, and display some or all of the received sensor measurements and processor-calculated data on the display. The App 202 may further calculate extended data, e.g., a Pulse Score 204 and Pulse Points 206, related to body conditions, health, activity targets and the like, and display the calculated data 206 on the display.

A Pulse Score 204 can be a scoring method to provide an indication to the user as a sense of the general state of their health, as an example, of where their health is compared relative to others. Pulse Score 204 can also allow the user to see how their behavior changes impact their own health. In some embodiments, improvements (for example, an increase) in Pulse Score 204, reflecting an improvement in health, are a way users can attain Pulse Points 206. Pulse Points 206 are a rewards system where an individual can use Pulse Score 204 to accumulate Pulse Points 206, which in turn, can provide, or be exchanged for, rewards for meeting goals. Accordingly, as the user improves/increases their Pulse Score 204 through making more sound health decisions, they can receive Pulse Points 206 that can be redeemed for prizes or discounts on purchases, e.g., purchases of health related items.

In some embodiments, the App 202 implements a portable algorithm, for providing the user a reflection of total health status by taking the basic outputs from the wearable apparatus 100 and converting that data into heart rate, oxygen saturation, pulse wave velocity, blood pressure, and activity.

Figure 5:
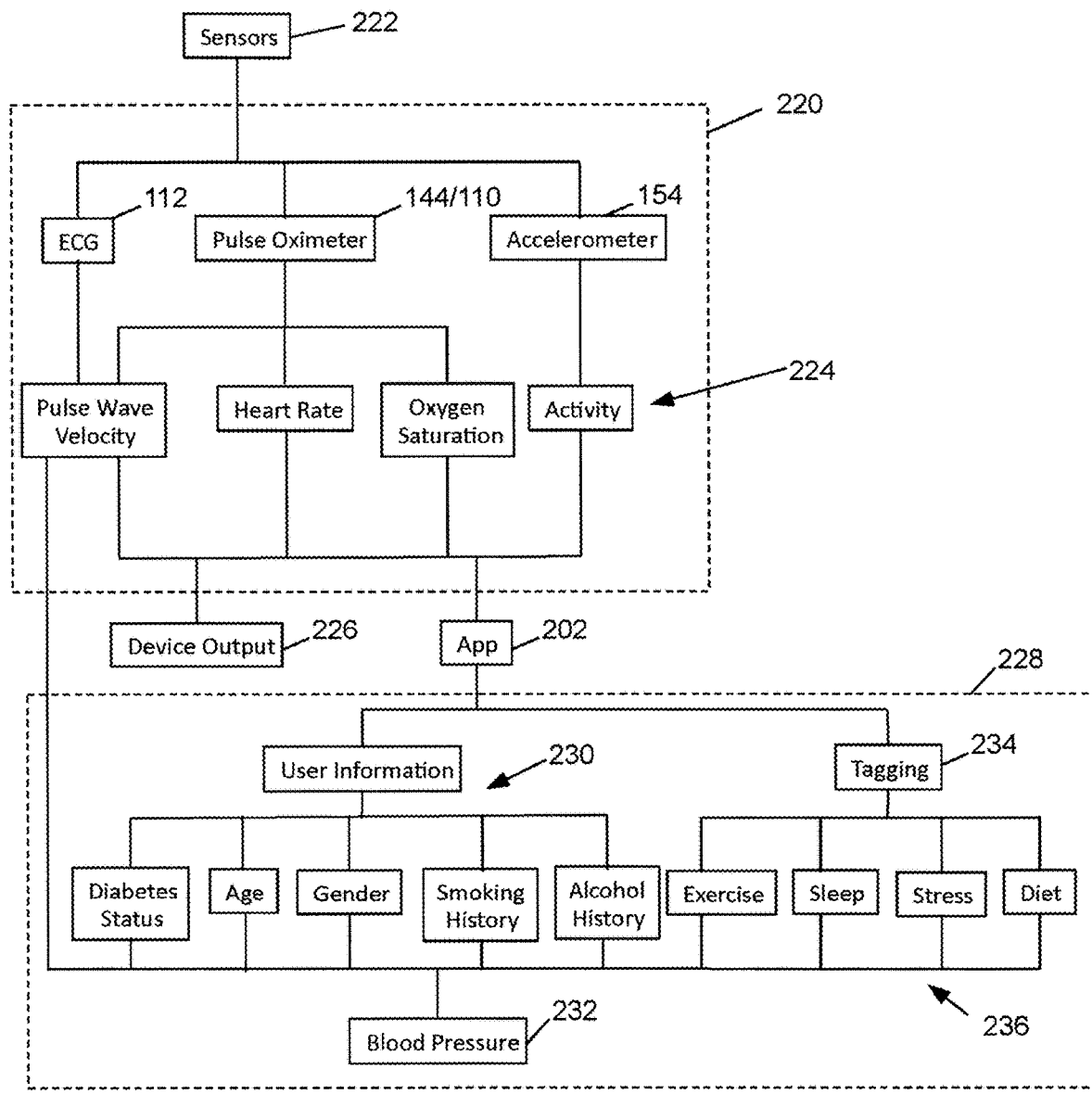
FIG. 5 is a diagram representation of embodiments of algorithms that can be used in association with a wearable electronic apparatus for monitoring and assessing an individual's cardiovascular health.

FIG. 5 shows the device algorithm 220, the portable algorithm 228 and the interaction therewith. As shown, the sensors 222 of the wearable apparatus 100, such as the ECG module 145, the Pulse Oximeter (Pulse LED 144 and light sensor 110) and the accelerometer 154, collects data of the user. The processor 142 uses the collected data to calculate the user's body and activity data 224 such as pulse wave velocity, heart rate, oxygen saturation and activity. The calculated body and activity data 224 may be output, e.g., displayed, at the output 226 of the apparatus 100. The output 226 may be an LCD/LED display on or integrated with the wearable apparatus 100 for displaying the output data in text or graphic form, or one or more LEDs (which may be considered as a simple display) on or integrated with the wearable apparatus 100 for displaying the output data using different combination of LED lights. In this embodiment, the wearable apparatus may not comprise a Bluetooth module 146.

Alternatively, the output data may be transmitted to the App 202 of a device 200 external or remote to the wearable apparatus 100 via, e.g., Bluetooth. The App 202 executes the portable algorithm 228, and uses the user's information 230 such as the user's historical health data, e.g., diabetes status, age, gender, smoking history, alcohol history and the like, to calculate blood pressure 232.

In some embodiments, the App 202 also comprises a tagging function 234 allowing automatically tagging (Autotagging) and/or manually tagging, where the output of the data readings and analysis can be subject to a tagging program where apparatus 100 can determine the user's behavior 236, such as eating, sleeping, working out, or is stressed, at a time point and attaching an electronic tag to that event.

Tagging 234 can be understood to be the taking of core health metrics from apparatus 100 and using analytics to determine if the user is involved in such behaviors 236 as eating, sleeping, resting, working out, or is stressed at a specific time and attaching a digital tag to that event.

Auto-tagging can be understood to be the automatic tagging of these events by the App 202. In some embodiments, the measures of heart rate, activity, pulse wave velocity, oxygen saturation, and/or blood pressure in combination with prior- or post-tagging can be used to accomplish auto-tagging, or to provide additional personal input or information. In order to adequately provide auto-tagging options heart rate and activity tracking can be used to be able to tell resting, exercising, and sleeping states. In some embodiments, the use of pulse wave velocity can allow for determination of fatty meals the user may have had and this information can be used for tagging/auto-tagging. An indication of stress can be found through changes in blood pressure and heart rate with minimal movement and this information can be used for tagging/auto-tagging.

In some embodiments, auto-tagging functions can be combined with a health trajectory output for the individual to predict a future state of health. These two features can provide the user with the reflection and foresight to start making better health decisions such as increased exercise, a better diet, improved sleeping habits, or increased awareness and response to stressors.

Accordingly, apparatus 100 and the methods of using the same can provide for the acquisition of more useful health metrics, a more convenient and user-friendly way to acquire measurements, and a mechanism to provide feedback to the user to generate thought and behavior change of the user with respect to their own health. The user can be provided with pertinent information that will help them make more informed health decisions. In some-embodiments, these health metrics can be captured as real-time information, at regular or pre-set intervals over the course of time, or at any time that the user wishes to apply.

In above embodiments, the wearable apparatus 100 collects data of the radial artery for calculating health metrics. However, in some alternative embodiments, the wearable apparatus 100 does not require data of the radial artery. Rather, the wearable apparatus 100 may locate its sensor(s) at any suitable body location along an artery where a pulse is detectable. For example, in various embodiments, the wearable apparatus 100 may locate its sensor(s) at a thumb, finger, ankle, toe, forehead and the like. For example, in one embodiment, the wearable apparatus 100 may be in the form of a headband.

In above embodiments, the wearable apparatus 100 comprises a single PCB 108. In some alternative embodiments, the wearable apparatus 100 comprises a plurality of rigid circuit boards 108 electrically coupled via suitable flexible electrical cables or wires. For example, in one embodiment, the wearable apparatus 100 comprises three rigid PCBs, with a first PCB receiving the charging circuit 152 and the accelerometer 154, a second PCB receiving the central chip 190 and the Bluetooth antenna, and a third PCB receiving the sensors and/or connectors of sensors, such as the ECG input 182 and the Pulse LED 144 and light sensor 110. In this embodiment, the second PCB is intermediate of the first and third PCBs.

Compared to the use of a single flexible circuit board, using multiple rigid circuit boards provides several advantages. For example, the rigid circuit boards provide sufficient protection to the components thereon. Further, by using above-described multiple PCBs 108, the electronic circuitry, including the PCBs 108 and components thereon, can be made with a small size and/or thickness for easily fitting into a rigid case 106.

In another embodiment, the wearable apparatus 100 is designed in a modularized manner for the ease of installing and replacing sensors. For example, the Pulse LED 144 and light sensor 110 in this embodiment are on a separate circuit board, which is connected to the PCB 108 via respective connectors on the circuit boards, and a flexible cable therebetween. The connectors are also modularized with standardized pins for connecting to different Pulse LEDs and light sensors.

In above embodiments, a suitable machine learning method is used to calculate blood pressure based some or all of the collected data and the user's historical health data. In an alternative embodiment, the blood pressure is calculated using the machine learning method based only on some or all of the collected data. No historical health data of the user is used. While the resulting blood pressure may not be as accurate as that calculated based on both the collected data and the user's historical health data, the resulting blood pressure may still have sufficient accuracy for the user to use.

In above embodiments, the sensors are arranged about an artery such as a distal radial artery. In some alternative embodiments, the sensors are arranged about a blood vessel, which may be a vein or an artery, depending on the implementation.

In above embodiments, the pulse oximeter comprises a pulse LED as a light emitter. In some other embodiments, any suitable light emitters may be alternatively used.

In above embodiments, the pulse LED or light emitter is used for detecting blood pulse wave and for detecting oxygen saturation, and the ECG sensor is used for detecting the start of pulse. In some alternative embodiments, a sonic sensor is used for detecting blood pulse wave. In some of these embodiments, no light emitter is used. However, a drawback of these embodiments is that the oxygen saturation may be undetectable.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

While the above description details certain embodiments of the invention and describes certain embodiments, no matter how detailed the above appears in text, the invention can be practiced in many ways. Details of the apparatuses and methods may vary considerably in their implementation details, while still being encompassed by the invention disclosed herein. These and other changes can be made to the invention in light of the above description.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification. Accordingly, the actual scope of the invention encompasses not only the disclosed embodiments, but also all equivalent ways of practicing or implementing the invention.

The above description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. The elements and acts of the various embodiments described above can be combined to provide further embodiments.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

REFERENCES

The following references are hereby incorporated by reference into this application in their entirety:

1. The Reference Values for Arterial Stiffness Collaboration, "Determinants of pulse wave velocity in healthy people and in the presence of cardiovascular risk factors: 'establishing normal and reference values'". European Heart Journal (2010) 31, 2338-2350 doi: 10.1093/euroheart/ehq165.

2. Augustine et al., "Effect of a Single Bout of Resistance Exercise on Arterial Stiffness Following a High-Fat Meal", Int J Sports Med; DOI: http://dx.doi.org/10.1055/s-0033-1363266 Copyright Georg Thieme Verlag, Stuttgart, New York (2014); ISSN 0172-4622.

3. Millasseau et al., "Determination of age-related increases in large artery stiffness by digital pulse contour analysis", Clinical Science (2002) 103, 371-377.

4. Firstbeat Technologies Ltd., "Stress and Recovery Analysis Method Based on 24-hour Heart Rate Variability", Published Sep. 16, 2014, updated Nov. 4, 2014.

5. Contini, R, "Body Segment Parameters, Part II", Artificial Limbs (1972), 16(1) 1-19.

What is claimed is:

1. An apparatus, comprising:
   a strap;
   a first connector at a first end of the strap;
   a second connector at a second end of the strap, the second connector configured to connect to the first connector to fasten the first end to the second end, directly, to configure the strap into a wristband, or indirectly, to configure the strap with a smartwatch into a smart wristwatch;
   a plurality of circuit boards at a middle portion of the strap, the plurality of circuit boards comprising:
      a first circuit board with a battery charging circuit attached to the first circuit board;
      a second circuit board with a microcontroller attached to the second circuit board; and
      a third circuit board with a pulse light emitting diode (LED) attached to the third circuit board and a light sensor attached to the third circuit board, wherein the light sensor and the pulse LED are parts of a pulse oximeter;
   a plurality of flexible electrical wires electrically coupling the plurality of circuit boards,
      wherein the second circuit board is intermediate to the first circuit board and the third circuit board,
      wherein an accelerometer is attached to the first circuit board,
      wherein a wireless communications antenna is attached to the second circuit board,
      wherein the pulse LED is configured to emit a first type of light and a second type of light,
      wherein the light sensor comprises respective components to sense the first type of light and the second type of light,
      wherein the first type of light has wavelengths within a first range of wavelengths and the second type of light has wavelengths within a second range of wavelengths, and
      wherein the pulse oximeter comprises a computing component configured to:
         compare a first reading sensed by the light sensor corresponding to an amount of the first type of light absorbed by blood of a user under skin of the user, corresponding to oxygenated blood, and a second reading sensed by the light sensor corresponding to an amount of the second type of light absorbed by the blood, corresponding to deoxygenated blood; and
         determine an amount of oxygen in the blood based on the comparison between the first reading and the second reading; and
   a second computing component communicatively coupled to the computing component and configured to predict a health metric of the user using machine learning and using the amount of oxygen in the blood as input for the machine learning.

2. The apparatus of claim 1, wherein the strap comprises:
   a first electrocardiogram (ECG) electrode facing inwardly when the strap is configured into a wristband or a wristwatch to allow the first ECG electrode to touch an anterior portion of the wrist of the user; and
   a second ECG electrode arranged to allow the second ECG electrode to be touched by a finger of an opposing hand of the user to complete a circuit across a heart of the user to produce an electrical output to make an ECG reading, when the strap is configured into a wristband or a wristwatch.

3. The apparatus of claim 1, wherein the machine learning uses supervised learning.

4. The apparatus of claim 3, wherein the machine learning comprises a neural network.

5. The apparatus of claim 4, wherein training output of the machine learning comprises a blood pressure for each input of the amount of oxygen in the blood.

6. The apparatus of claim 5, wherein a final layer of the neural network consists of a single neuron with an output intensity that maps to the blood pressure.

7. The apparatus of claim 5, wherein a final layer of the neural network consists of a group of neurons with an output representing a range of the blood pressure.

8. The apparatus of claim 1, wherein the machine learning uses supervised learning and comprises a polynomial regression analysis method.

9. An apparatus, comprising:
a strap;
a first connector at a first end of the strap;
a second connector at a second end of the strap, the second connector configured to connect to the first connector to fasten the first end to the second end, directly, to configure the strap into a wristband, or indirectly, to configure the strap with a smartwatch into a smart wristwatch;
a plurality of circuit boards at a middle portion of the strap, the plurality of circuit boards comprising:
 a first circuit board with a battery charging circuit attached to the first circuit board;
 a second circuit board with a microcontroller attached to the second circuit board; and
 a third circuit board with
  a first electrocardiogram (ECG) electrode attached to the third circuit board and facing inwardly when the strap is configured into a wristband or a wristwatch to allow the first ECG electrode to touch an anterior portion of a wrist of a user,
  a second ECG electrode attached to the third circuit board and arranged to allow the second ECG electrode to be touched by a finger of an opposing hand of the user to complete a circuit across a heart of the user to produce an electrical output to make an ECG reading, when the strap is configured into a wristband or a wristwatch, and
  a pulse oximeter attached to the third circuit board, wherein the pulse oximeter comprises a pulse light emitting diode (LED) attached to the third circuit board and a light sensor attached to the third circuit board;
a plurality of flexible electrical wires electrically coupling the plurality of circuit boards,
 wherein an accelerometer is attached to the first circuit board,
 wherein a wireless communications antenna is attached to the second circuit board,
 wherein the pulse LED is configured to emit a first type of light and a second type of light,
 wherein the light sensor comprises respective components to sense the first type of light and the second type of light,
 wherein he first type of light has wavelengths within a first range of wavelengths and the second type of light has wavelengths within a second range of wavelengths, and
 wherein the pulse oximeter comprises a computing component configured to:
  compare a first reading sensed by the light sensor corresponding to an amount of the first type of light absorbed by blood of the user under skin of the user, corresponding to oxygenated blood, and a second reading sensed by the light sensor corresponding to an amount of the second type of light absorbed by the blood, corresponding to deoxygenated blood; and
  determine an amount of oxygen in the blood based on the comparison between the first reading and the second reading; and
a second computing component communicatively coupled to the computing component and configured to predict a health metric of the user using machine learning and using the amount of oxygen in the blood and the ECG reading as inputs for the machine learning.

10. The apparatus of claim 9, wherein the machine learning uses supervised learning.

11. The apparatus of claim 10, wherein the machine learning comprises a neural network.

12. The apparatus of claim 11, wherein training output of the machine learning comprises a blood pressure for each combination of inputs of the ECG reading and the amount of oxygen in the blood.

13. The apparatus of claim 12, wherein a final layer of the neural network consists of a single neuron with an output intensity that maps to the blood pressure.

14. The apparatus of claim 12, wherein a final layer of the neural network consists of a group of neurons with an output representing a range of the blood pressure.

15. The apparatus of claim 9, wherein the machine learning uses supervised learning and comprises a polynomial regression analysis method.

16. An apparatus, comprising:
a strap;
a first connector at a first end of the strap;
a second connector at a second end of the strap, the second connector configured to connect to the first connector to fasten the first end to the second end, directly, to configure the strap into a wristband, or indirectly, to configure the strap with a smartwatch into a smart wristwatch;
a plurality of circuit boards at a middle portion of the strap, the plurality of circuit boards comprising;
 a first circuit board with a battery charging circuit attached to the first circuit board;
 a second circuit board with a microcontroller attached to the second circuit board; and
 a third circuit board with a pulse light emitting diode (LED) and a light sensor attached to the third circuit board,
  wherein the light sensor and the pulse LED are parts of a pulse oximeter,
  wherein when the strap is configured into a wristband or a wristwatch around a wrist of a user, the light sensor is configured to sense light passing through openings in the strap which was reflected off of a peripheral artery of the wrist of the user and originating from the pulse LED, and
  wherein the second circuit board is intermediate to the first circuit board and the third circuit board;
a plurality of flexible electrical wires electrically coupling the plurality of circuit boards,
 wherein an accelerometer is attached to the first circuit board,
 wherein a wireless communications antenna is attached to the second circuit board,
 wherein the pulse LED is configured to emit a first type of light and a second type of light,
 wherein the light sensor comprises respective components to sense thefirst type of light and the second type of light,
 wherein the first type of light has wavelengths within a first range of wavelengths and the second type of light has wavelengths within a second range of wavelengths, and
 wherein the pulse oximeter comprises a computing component configured to:
  compare a first reading sensed by the light sensor corresponding to an amount of the first type of light absorbed by blood of the user under skin of the user, corresponding to oxygenated blood, and a second reading sensed by the light sensor corresponding to an amount of the second type of light absorbed by the blood, corresponding to deoxygenated blood; and determine an amount of oxygen in the blood based on the comparison between the first reading and the second reading; and a second computing component communicatively coupled to the computing component and configured to predict a health metric of the user using machine learning and using the amount of oxygen in the blood as input for the machine learning.

17. The apparatus of claim 16, wherein the machine learning uses supervised learning.

18. The apparatus of claim 17, wherein the machine learning comprises a neural network.

19. The apparatus of claim 18, wherein training output of the machine learning comprises a blood pressure for each combination of inputs of the ECG reading and the amount of oxygen in the blood.

20. The apparatus of claim 19, wherein a final layer of the neural network consists of a single neuron with an output intensity that maps to the blood pressure.

21. The apparatus of claim 19, wherein a final layer of the neural network consists of a group of neurons with an output representing a range of the blood pressure.

22. The apparatus of claim 16, wherein the machine learning uses supervised learning and comprises a polynomial regression analysis method.

23. An apparatus, comprising:

a strap;

a first connector at a first end of the strap;

a second connector at a second end of the strap, the second connector configured to connect to the first connector to fasten the first end to the second end, directly, to configure the strap into a wristband, or indirectly, to configure the strap with a smartwatch into a smart wristwatch;

a plurality of circuit boards at a middle portion of the strap, the plurality of circuit boards comprising;

a first circuit board with a battery charging circuit attached to the first circuit board;

a second circuit board with a microcontroller attached to the second circuit board; and a third circuit board with a pulse light emitting diode (LED) and a light sensor attached to the third circuit board, wherein the light sensor and the pulse LED are parts of a pulse oximeter, wherein when the strap is configured into a wristband or a wristwatch around a wrist of a user, the light sensor is configured to sense light passing through openings in the strap which was reflected off of a peripheral artery of the wrist of the user and originating from the pulse LED, wherein a first electrocardiogram (ECG) electrode and a second ECG electrode are attached to one of the boards of the plurality of circuit boards, and wherein the second circuit board is intermediate to the first circuit board and the third circuit board;

a plurality of flexible electrical wires electrically coupling the plurality of circuit boards, wherein an accelerometer is attached to the first circuit board, wherein a wireless communications antenna is attached to the second circuit board, wherein the pulse LED is configured to emit a first type of light and a second type of light, wherein the light sensor comprises respective components to sense the first type of light and the second type of light.

wherein the first type of light has wavelengths within a first range of wavelengths and the second type of light has wavelengths within a second range of wavelengths, and wherein the pulse oximeter comprises a computing component configured to:

compare a first reading sensed by the light sensor corresponding to an amount of the first type of light absorbed by blood of the user under skin of the user corresponding to oxygenated blood, and a second reading sensed by the light sensor corresponding to an amount of the second type of light absorbed by the blood, corresponding to deoxygenated blood; and determine an amount cif oxygen in the blood based on the comparison between the first reading and the second reading; and a second computing component communicatively coupled to the computing component and configured to predict a health metric of the user using machine learning and using the amount of oxygen in the blood and an ECG reading, based on outputs of the first ECG electrode and the second ECG electrode, as inputs for the machine learning.

24. The apparatus of claim 23, wherein the machine learning uses supervised learning.

25. The apparatus of claim 24, wherein the machine learning comprises a neural network.

26. The apparatus of claim 25, wherein training output of the machine learning comprises a blood pressure for each combination of inputs of the ECG reading and the amount of oxygen in the blood.

27. The apparatus of claim 26, wherein a final layer of the neural network consists of a single neuron with an output intensity that maps to the blood pressure.

28. The apparatus of claim 26, wherein a final layer of the neural network consists of a group of neurons with an output representing a range of the blood pressure.

29. The apparatus of claim 23, wherein the machine learning uses supervised learning and comprises a polynomial regression analysis method.

* * * * *